United States Patent [19]

Kientzler

[11] Patent Number: Plant 6,684

[45] Date of Patent: Mar. 21, 1989

[54] IMPATIENS PLANT NAMED AGLIA

[75] Inventor: Ludwig Kientzler, Bad Kreuznach, Fed. Rep. of Germany

[73] Assignee: Paul Ecke, Jr., Encinitas, Calif.

[21] Appl. No.: 119,437

[22] Filed: Nov. 12, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An impatiens plant named Aglia having large bright reddish-purple flowers, green leaves with yellow variegation extending from the mid vein, upright growth habit with very good self branching, and its early flowering and floriferous habits.

1 Drawing Sheet

The present invention relates to a new and distinct cultivar of impatiens plant known by the cultivar name Aglia, and botanically known as impatiens.

Aglia was developed by applicant through a controlled breeding program in Bad Kreuznach, Federal Republic of Germany. Both the male and female parents are unknown at this time. Aglia was discovered and selected as one flowering plant within the progeny of the cross by applicant in a controlled environment in Bad Kreuznach, Federal Republic of Germany.

The first act of asexual reproduction of Aglia was accomplished when terminal or stem cuttings were taken from the initial selection by applicant in a controlled environment in Bad Kreuznach, Federal Republic of Germany. Horticultural examination of selected plants of Aglia has demonstrated that the combination of characteristics as herein disclosed for Aglia are firmly fixed and are retained through successive generations of asexual reproduction.

Aglia has not been observed under all possible environmental conditions. The phenotype may vary significantly with variations in environment such as temperature, light intensity, soil conditions, nutrient feeding, and day length.

The following characteristics distinguish the new impatiens from both its parent varieties and other cultivated impatiens of this type known and used in the floriculture industry within the knowledge of applicant:

1. Large bright reddish-purple flowers.
2. Green leaves with yellow variegation on either side of the mid vein of older leaves.
3. The plant flowers very early and is floriferous, with large flowers covering the foliage abundantly.
4. The growth habit is upright with very good self branching; medium height.

The accompanying colored photograph illustrates in perspective view the overall appearance of this cultivar, with colors being as true as it is reasonable possible to obtain in a colored reproduction of this type.

The following is a detailed description of Aglia based on plants produced under commercial practice in Encinitas, Calif. Unrooted cuttings were rooted in March under intermittent mist, and the plants subsequently transplanted to 6" pots. Flowering commenced in July, and a plant nicely proportioned for a 6" pot was ready five or six weeks later. Most of the data which follows was collected between Sept. 1–5 in Encinitas, Calif. The measurements and description of foliage were taken from fully expanded leaves.

Color references are made to The Royal Horticultural Society Colour Chart except where general terms of ordinary dictionary significance are used. Color chart correlations were made indoors but under natural light conditions, with the leaves and flowers being compared to the R.H.S. color chart near a west-face window.

Parentage: Seedling from cross pollination, with both the male and female parents being unknown at this time.

Propagation:

*Type cutting.*—Tip cutting. Stems 2–3 cm long will develop to 4–5 cm after 21 days in propagation.

*Time to initiate roots.*—8–10 days at 73° C. Nicely developed root mass in 18–21 days.

*Rooting habit.*—Numerous, fibrous adventitious roots from the stem.

Plant description:

*Form.*—Symmetrical, bush shaped, flowering herb, with self-branching characteristics giving the plant a full appearance.

*Habit of growth.*—Vigorous, self-branching, upright habit, producing whorls of leaves and flowers on branched stems. Growth is indeterminate and flowering is continuous.

*Foliage description.*—Leaves are simple. Lower leaves on stem are opposite. Higher leaves in whorls of 5. Leaf shape: Elliptic; acuminate tip and attenuate base. Leaf blade size: 10–11 cm×3.5–4 cm. Leaf margin: Ciliate and finely serrated. Leaf texture: Upper surface: glabrous. Under surface: glabrous. Leaf color: Green with reddish mid vein. Older leaves with yellow variegation at the base and either side of the mid vein. Upper surface: Near 137A. Under surface: Near 138B. Venation: Pinnate, with reddish veins on under surface.

Flowering description:

*Flowering habits.*—Very floriferous, flowering continuously. Flowers develop progressively around the whorl of leaves, taking 5–7 days from buds which show color to bloom. Flowers are single and large, lasting for 2–3 weeks.

*Natural flowering season.*—Flowering is indeterminate and occurs throughout the year. Quantity of flowers increases with increasing light intensity and duration.

*Flower buds.*—Ellipsoidal and covered with 3 sepals. A reddish approximately 4.5 cm long spur originates from the base of the major sepal. Two additional, rudimentary sepals are fused to back of the top petal.

*Flower borne.*—Singly, on pedicels 2.5–3.5 cm long, pedicels reddish in color.

*Quantity of flowers.*—Floriferous. Two flowers per leaf occurring progressively around the whorl of leaves so that tight buds to mature blooms are visible at the same time in large numbers.

*Petals.*—Number of petals: Five (5). Shape: Top petal heart shaped with wide base, all other petals heart shaped with pointed base. All petals overlap. Color: Upper surface: 57B. Under surface: 58B. Size of flowers: 5–5.5 cm.

*Reproductive organs.*—Stamens: Five (5) with the lower stamen being shorter than the other stamens. Stamens united in an asymmetrical tube surrounding the ovary. Anthers: Hooded, cream fused with red. Pollen: Cream color. Stigma: Five pointed star, colorless. Styles: Very short, reddish in color. Ovary: 5 celled, 4–5 mm long until fertilized, green in color.

I claim:

1. A new and distinct cultivar of impatiens plant named Aglia, as illustrated and described, and parts thereof.

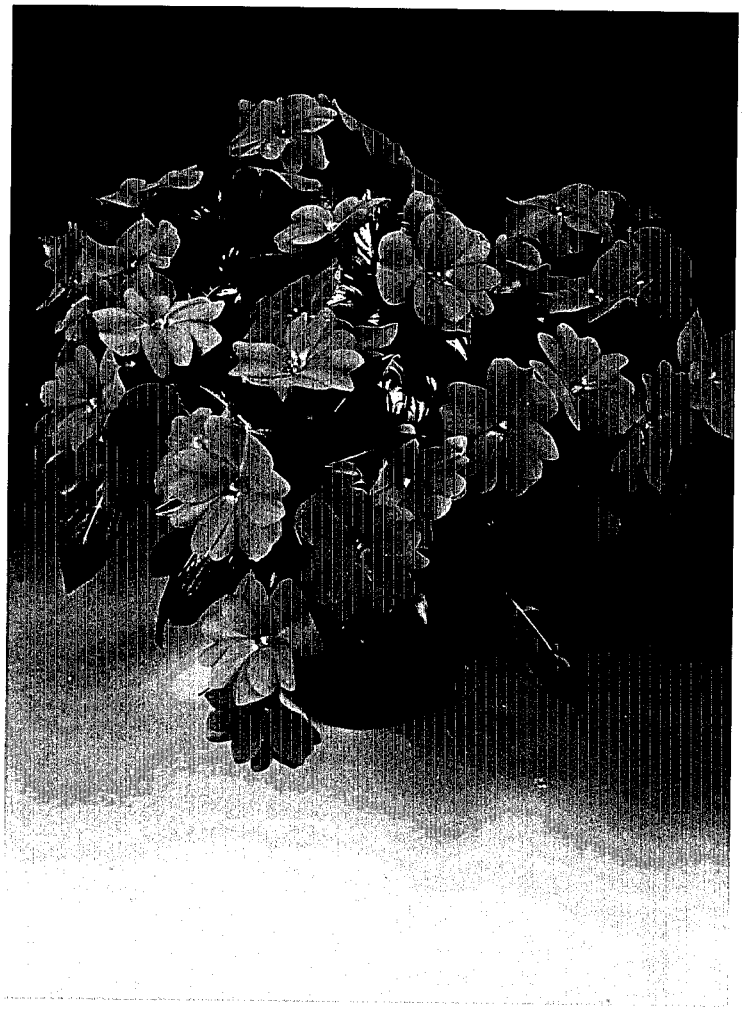

* * * * *